US007742561B2

(12) United States Patent
Ueki

(10) Patent No.: US 7,742,561 B2
(45) Date of Patent: Jun. 22, 2010

(54) IMAGING APPARATUS

(75) Inventor: Hironori Ueki, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 177 days.

(21) Appl. No.: 12/030,930

(22) Filed: Feb. 14, 2008

(65) Prior Publication Data

US 2008/0279330 A1  Nov. 13, 2008

(30) Foreign Application Priority Data

May 8, 2007  (JP) ............................. 2007-123709

(51) Int. Cl.
*G01N 23/04* (2006.01)
*A61B 6/04* (2006.01)
(52) U.S. Cl. .......................................... 378/63; 378/37
(58) Field of Classification Search .................... 378/37, 378/62, 63, 98.8, 98.12, 114–116; 250/370.09, 250/370.11, 366–368; 600/425, 427
See application file for complete search history.

(56) References Cited

U.S. PATENT DOCUMENTS

| 5,419,320 | A | * | 5/1995 | Kawaguchi et al. .......... 600/425 |
| 5,453,611 | A | * | 9/1995 | Oozu et al. .............. 250/208.1 |
| 5,803,082 | A | * | 9/1998 | Stapleton et al. ............ 600/407 |
| 5,812,629 | A | * | 9/1998 | Clauser ...................... 378/62 |
| 5,929,434 | A | * | 7/1999 | Kozlowski et al. ....... 250/214 A |
| 6,901,134 | B2 | * | 5/2005 | Nascetti et al. ............ 378/98.8 |
| 7,198,404 | B2 | * | 4/2007 | Navab et al. ................ 378/206 |
| 7,214,944 | B2 | * | 5/2007 | Rostaing et al. ........ 250/370.06 |
| 7,372,935 | B2 | * | 5/2008 | Bernhardt et al. .............. 378/4 |
| 7,436,927 | B2 | * | 10/2008 | Hempel ....................... 378/63 |

FOREIGN PATENT DOCUMENTS

WO    WO 98/24361    6/1998

OTHER PUBLICATIONS

David A. Boas et al., "Imaging the Body with Diffuse Optical Tomography," IEEE Signal Processing Magazine, vol. 18, No. 6, pp. 57-75, (Nov. 2001).
Hawrysz D. J. et al., "Developments Toward Diagnostic Breast Cancer Imaging Using Near-Infrared Optical Measurements and Fluorescent Contrast Agents," Neoplasia, vol. 2, No. 5, pp. 388-417 (30), (Sep.-Oct. 2001).

* cited by examiner

*Primary Examiner*—Edward J Glick
*Assistant Examiner*—Thomas R Artman
(74) *Attorney, Agent, or Firm*—Antonelli, Terry, Stout & Kraus, LLP.

(57) ABSTRACT

The present invention is designed to overcome the disadvantages of X-ray imaging having difficulty in high-sensitivity measurement and of optical imaging having difficulty in high-spatial-resolution measurement, when used for diagnostic purposes. The present invention provides an imaging apparatus including an X-ray tube, a detector having sensitivity to X-rays and light, and a processing unit that processes the result of detection. In the imaging apparatus, the processing unit processes, as a first signal, a signal detected by the detector during an irradiation period in which an X-ray source provides X-ray irradiation, and processes, as a second signal, a light signal detected by the detector during a period other than the irradiation period.

18 Claims, 12 Drawing Sheets

IMAGING APPARATUS

CLAIM OF PRIORITY

The present application claims priority from Japanese application JP 2007-123709 filed on May 8, 2007, the content of which is hereby incorporated by reference into this application.

BACKGROUND OF THE INVENTION

1. Field of the Invention

The present invention relates to an imaging apparatus that uses X-rays and light to make a measurement on a living body, for use in the field of diagnostic instruments intended mainly for purposes of early diagnosis of disease such as cancer.

2. Description of the Related Art

A mammography apparatus is developed as a device for early detection of breast cancer and is widely used for examination for breast cancer or the like. The mammography apparatus is an X-ray machine intended solely for the breast and is capable of detecting tiny calcification developed around a tumor or a cancer cell.

A method for imaging the inside of a cloudy medium such as the breast, using light, is reported in Japanese Patent Translation Publication No. 2001-510361. The method irradiates the breast with the light, and measures the light scattered within the breast. Then, the method calculates the absorption distribution of the light within the breast, on the basis of the measured data. The method exploits, in particular, the property that blood absorbs the light intensely so as to detect a nutritional blood vessel formed around a cancer cell. A method such as Diffuse Optical Tomography (DOT) described for example in David A. Boas et al., "Imaging the Body with Diffuse Optical Tomography," IEEE Signal Processing Magazine, Vol. 18, No. 6, pp. 57-75, (2001) is used as a method for calculating an optical absorption distribution in a living body, on the basis of measured data on scattered light.

A method intended mainly for a living body such as a small animal is developed and widely used. This method involves administering a fluorescent molecular probe or a luminescent molecular probe into the living body, and measuring a distribution thereof within the living body. The fluorescent molecular probe and the luminescent molecular probe can provide selectivity for a target molecule unusually formed by a tumor or the like. Accordingly, these probes have the merit of being capable of making a high-sensitive measurement on a tiny cancer cell. Currently, various types of fluorescent molecular probes using fluorescent proteins, fluorescent nanoparticles, or the like, or luminescent molecular probes using luciferase are developed. A method intended for purposes of detection of breast cancer, which involves administering a fluorescent molecular probe into the human body and performing imaging using DOT, is tried and reported in Hawrysz D. J. et al., "Developments Toward Diagnostic Breast Cancer Imaging Using Near-Infrared Optical Measurements and Fluorescent Contrast Agents," Neoplasia, Vol. 2, No. 5, pp. 388-417 (30), (2001).

SUMMARY OF THE INVENTION

A mammography apparatus is capable of making a measurement with high spatial resolution on the order of a few tens of micrometers and is effective particularly in detecting tiny calcification. However, the reading of a mammographic image generally requires high skill and thus involves the problem that a pathological change is overlooked. Also, the reading takes much time and thus involves the problem that there is a heavy load on a doctor who reads X-rays.

Breast imaging using light has the advantage of causing no X-radiation exposure as compared to the mammography apparatus. However, the breast imaging has the problem of having difficulty in locating a pathological change because of having a low spatial resolution of the order of a few millimeters to a few centimeters. Moreover, breast imaging using a fluorescent molecular probe or a luminescent molecular probe has the advantage of having high sensitivity for detection of a pathological change. However, the breast imaging has the problem of having difficulty in locating a pathological change because of having a low spatial resolution of the order of a few millimeters to a few centimeters. Such deterioration in the spatial resolution is caused by light scattering within the breast, and thus, various attempts are made to improve a DOT algorithm. However, it is generally difficult to enhance the spatial resolution of body imaging using light.

A summary of means adopted by the present invention is as follows.

First Means

There is provided an imaging apparatus, which includes an X-ray source, a first detector, and a processing unit. The X-ray source irradiates a subject with X-rays. The first detector faces the X-ray source with the subject in between, and detects the X-rays and light. The processor processes the result of detection by the first detector. The processing unit processes, as a first signal, an X-ray signal detected by the first detector during an irradiation period in which the X-ray source provides X-ray irradiation, and processes, as a second signal, a light signal detected by the first detector during a period other than the irradiation period. Thereby, X-ray imaging and optical imaging using a luminescent molecular probe can be achieved by a single examination. When a breast is a subject to be examined, a mammographic image of high spatial resolution and an optical image of high pathological change detectivity can be obtained by the single examination. Accordingly, a combination of advantages of both images enables reducing the overlooking of pathological change and the load of the reading of X-rays, thus enhancing diagnostic power.

Second Means

Provided is the imaging apparatus according to the first means, in which a photodetector of the first detector is made of a photoconductive material having sensitivity to light of the X-ray wavelength range to the infrared wavelength range inclusive. Thereby, a single detector can be used to detect both the X-rays and the light.

Third Means

Provided is the imaging apparatus according to the first means, in which the photodetector of the first detector is made of a scintillator material. The scintillator material transmits some of light of the visible wavelength range to the infrared wavelength range inclusive. The scintillator converts the X-ray signal into the light signal, and thus, an optical sensor can be used for the X-ray imaging. Also, the light exiting from the subject can pass through the scintillator and be detected by the optical sensor, and thus, the single detector can be used to detect both the X-rays and the light.

Fourth Means

Provided is the imaging apparatus according to the first means, in which the first detector is formed of two layers: an X-ray detection layer having sensitivity to the X-rays and a photodetection layer having sensitivity to the light of the visible wavelength range to the infrared wavelength range inclusive. The light exiting from the subject is detected by the photodetection layer, and also, the X-rays exiting from the subject pass through the photodetection layer and are then detected by the X-ray detection layer. Thereby, the single detector can be used to detect both the X-rays and the light.

Fifth Means

Provided is the imaging apparatus according to the first means, further including a light guide that guides the light exiting through the outer surface of the subject to a photodetection surface of the first detector. This enables preventing defocusing resulting from the diffusion of the light in space between the surface of the subject and the first detector, thus preventing deterioration in the spatial resolution of the optical imaging.

Sixth Means

Provided is the imaging apparatus according to the fifth means, in which the light guide has the function of eliminating some of the X-rays scattered within the subject. This enables preventing deterioration in the spatial resolutions of both the X-ray imaging and the optical imaging.

Seventh Means

Provided is the imaging apparatus according to the first means, in which the processing unit has the function of combining the first signal and the second signal into one image. This enables seeing the X-ray image and the optical image on one and the same image, thus making the relative positions of these images clear. Accordingly, the overlooking of pathological change and the load of the reading of X-rays can be reduced.

Eighth Means

Provided is the imaging apparatus according to the first means, further including a light source that irradiates the subject with the light of the ultraviolet wavelength range to the infrared wavelength range inclusive. Thereby, besides the X-ray imaging, blood vessel imaging using the light and optical imaging using a fluorescent molecular probe can be achieved by a single examination.

Ninth Means

Provided is the imaging apparatus according to the eighth means, including a support that supports the subject while being in contact with the subject. The support has the light guide function of guiding the light emitted from the light source to the subject. This enables reducing the reflection of the light bouncing off the surface of the subject, thus preventing a reduction in the intensity of the light entering into the subject.

Tenth Means

Provided is the imaging apparatus according to the first means, further including a second detector that detects the light, the second detector being disposed between the X-ray source and the subject. Also in the imaging apparatus, the processing unit processes, as a first signal, a light signal detected by the first detector during an irradiation period in which the X-ray source provides X-ray irradiation, and processes signals detected by the first detector and the second detector during a period other than the irradiation period, as a second signal and a third signal, respectively. Thereby, the light exiting through the surface of the subject on the opposite side to the side on which the first detector is disposed can be detected by the second detector. This enables enlarging the taking range of the optical imaging, thus enhancing the sensitivity.

Eleventh Means

Provided is an imaging apparatus, which includes an X-ray source that irradiates a subject with X-rays; a first detector that detects the X-rays, the first detector facing the X-ray source with the subject in between; a second detector that detects light, the second detector being disposed between the X-ray source and the subject; a third detector that detects the light, the third detector being disposed between the subject and the first detector; and a processing unit that processes the results of detection by the first to third detectors. In the imaging apparatus, the processing unit processes, as a first signal, an X-ray signal detected by the first detector during an irradiation period in which the X-ray source provides X-ray irradiation, and produces light signals detected by the third detector and the second detector during a period other than the irradiation period, as a second signal and a third signal, respectively. Thereby, the first detector takes a measurement of the X-ray image, while the third and second detectors can detect the light exiting through the surfaces of the subject on the side on which the first detector is disposed and on the opposite side thereto, respectively. This enables a combination of the X-ray image and two optical images, thus reducing the overlooking of pathological change and the load of the reading of X-rays, and thus enhancing the diagnostic power.

Twelfth Means

Provided is the imaging apparatus according to any one of the tenth and eleventh means, in which the processing unit has the function of combining the first signal, the second signal, and the third signal into one image. This enables seeing the X-ray image and the two optical images on one and the same image, thus making the relative positions of these images clear, and thus reducing the overlooking of pathological change and reducing the load of the reading of X-rays.

Thirteenth Means

Provided is the imaging apparatus according to the eleventh means, further including a reflecting mirror disposed between the X-ray source and the subject; a lens that focuses the light reflected from the reflecting mirror; and a second detector that detects the light focused by the lens. In the imaging apparatus, the processing unit produces, as a first signal, an X-ray signal detected by the first detector during an irradiation period in which the X-ray source provides X-ray irradiation, and produces light signals detected by the first detector and the second detector during a period other than the X-ray irradiation period, as a second signal and a third signal, respectively. Thereby, the light exiting through the surface of the subject on the opposite side to the side on which the first detector is disposed can be detected by the second detector. This enables enlarging the taking range of the optical imaging, thus enhancing the sensitivity.

Fourteenth Means

Provided is an imaging apparatus, which includes an X-ray source that irradiates a subject with X-rays; a first detector that detects the X-rays, the first detector facing the X-ray source with the subject in between; a first reflecting mirror disposed between the X-ray source and the subject; a first lens that focuses light reflected from the first reflecting mirror; a second detector that detects the light focused by the first lens; a second reflecting mirror disposed between the subject and the first detector; a second lens that focuses the light reflected from the second reflecting mirror; a third detector that detects the light focused by the second lens; and a processing unit that processes the results of detection by the first to third detectors. In the imaging apparatus, the processing unit processes, as a first signal, an X-ray signal detected by the first detector during an irradiation period in which the X-ray source provides X-ray irradiation, and processes light signals detected by the third detector and the second detector during a period other than the X-ray irradiation period, as a second signal and a third signal, respectively. Thereby, the first detector takes a measurement of the X-ray image, while the third and second detectors can detect the light exiting through the surfaces of the subject on the side on which the first detector is disposed and on the opposite side thereto, respectively. This enables a combination of the X-ray image and two optical images, thus reducing the overlooking of pathological change and the load of the reading of X-rays, and thus enhancing the diagnostic power.

Fifteenth Means

Provided is the imaging apparatus according to any one of the thirteenth and fourteenth means, further including a size measurement means for measuring the size of the subject, and a focus adjusting unit that adjusts the focus of the lens by changing the arrangement of the lens according to the result of measurement by the size measurement means. This enables preventing defocusing resulting from variations in the size of the subject, thus preventing deterioration in the spatial resolution of the optical imaging.

Sixteenth Means

Provided is the imaging apparatus according to any one of the thirteenth and fourteenth means, in which the processing unit has the function of combining the first signal, the second signal, and the third signal into one image. This enables seeing the X-ray image and the two optical images on one and the same image, thus making the relative positions of these images clear, and thus reducing the overlooking of pathological change and the load of the reading of X-rays.

Seventeenth Means

Provided is the imaging apparatus according to the sixteenth means, further including a size measurement means for measuring the size of the subject. In the imaging apparatus, the processing unit has the function of adjusting the combined position of the first signal and the third signal according to the result of measurement by the size measurement means. On the occasion of combination of the X-ray image and the optical image, this enables preventing a misalignment between the images resulting from variations in the size of the subject, thus improving the accuracy of position.

Eighteenth Means

Provided is the imaging apparatus according to any one of the tenth, eleventh, thirteenth and fourteenth means, in which the processing unit has the function of calculating luminescence or optical absorption intensity distribution within the subject, on the basis of the second signal and the third signal. Thereby, in addition to the X-ray image, the luminescence or optical absorption intensity distribution within the subject can be obtained by a single examination. This enables estimation of the location of a pathological change within the subject, thus enhancing the diagnostic power.

Nineteenth Means

Provided is the imaging apparatus according to any one of the tenth, eleventh, thirteenth and fourteenth means, in which the processing unit has the function of calculating a virtual signal by integrating the luminescence or optical absorption intensity distribution on an X-ray beam path within the subject, and the function of combining the first signal and the virtual signal into one image. This enables forming a virtual image of the luminescence intensity distribution or the optical absorption intensity distribution projected with respect to a virtual X-ray source, and also enables superimposing the virtual image on the X-ray image. As a result, a misalignment between the images can be prevented, and also the spatial resolution of the optical image can be enhanced.

According to the present invention, the X-ray imaging and the optical imaging can take place substantially simultaneously, while keeping the relative position of the subject. This facilitates merging the X-ray image of high spatial resolution and the optical image of high sensitivity, and thus enables the detection of pathological change and the reduction of overlooking thereof which have hitherto been difficult, thus enhancing the diagnostic power.

DETAILED DESCRIPTION OF THE PREFERRED EMBODIMENTS

Embodiments of the present invention will be described in detail below with reference to the drawings.

First Embodiment

Figure 1:
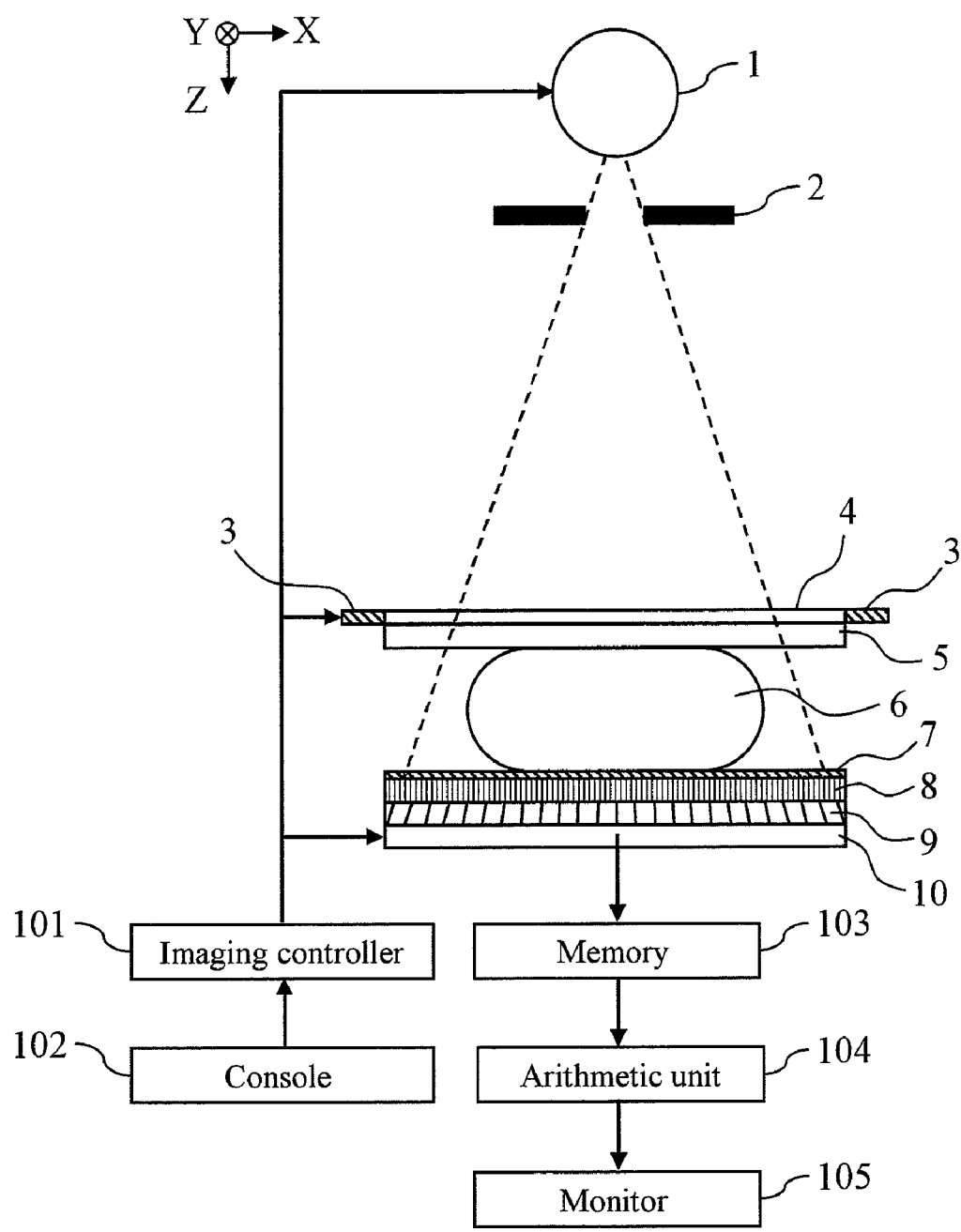
FIG. 1 is a schematic view of an imaging apparatus according to a first embodiment of the present invention.

FIG. 1 is a schematic view of an imaging apparatus according to a first embodiment of the present invention. Incidentally, a direction horizontal to a sheet of FIG. 1, a direction perpendicular to the sheet, and a direction from top to bottom of the sheet will be hereinafter referred to as an X direction, a Y direction, and a Z direction, respectively. The imaging apparatus according to the first embodiment is configured of an X-ray tube 1, a collimator 2, a light source 3, an optical diffuser 4, a compression paddle 5, an optical filter 7, a light guide plate 8, a scattered-ray elimination grid 9, a detector 10, an imaging controller 101, a console 102, a memory 103, an arithmetic unit 104, a monitor 105, and so on. Incidentally, a subject 6 which the imaging apparatus as defined in the first embodiment is intended for is the breast.

The X-ray tube 1 is a known X-ray tube for use in a mammography apparatus. The collimator 2 is a known collimator that serves to limit the range of X-ray irradiation irradiated by the X-ray tube 1 to the X direction and the Y direction. The above-described range of irradiation is generally set so that X-rays are applied to a region identical with an X-ray detection surface of the detector 10. However, the range of irradiation may be changed according to diagnostic purposes. The compression paddle 5 and the optical diffuser 4 are each in the form of a sheet in an XY plane. The optical diffuser 4 is adhesively disposed on the top surface of the compression paddle 5. The compression paddle 5 is a colorless, transparent sheet and is made of acrylic, glass, or the like. The light source 3 is disposed fixedly to the optical diffuser 4, as being in contact with each end face of the optical diffuser 4 in the X direction.

The light source 3 is provided for the purpose of applying excitation light to a fluorescent molecular probe administered into the subject 6, as will be described later. The light source 3 is used also as a light source of irradiation for optical absorption imaging on the subject 6, as will be described later. A representative example of a light emitting device for use in the light source 3 is a light-emitting diode (LED). Plural LEDs are disposed in the Y direction on both end faces of the optical diffuser 4 in the X direction. The light source 3 is removable from the optical diffuser 4, and light sources of varying wavelengths may be used for replacement according to what purpose the light source is used for. Incidentally, it is to be understood that the configuration of the light source 3 mentioned above is not limited to this embodiment. For example, plural LED light sources of varying wavelengths may be disposed in advance so that a user can select between the wavelengths according to what purpose the light source is used for. A known light source such as a xenon lamp may be also used in place of the LED. A known diffuser for use in backlighting for a liquid crystal display or the like is used as the optical diffuser 4.

Light emitted from the light source 3 is substantially uniformly diffused into the optical diffuser 4 in the X and Y directions. Then, the light travels in the Z direction out of the optical diffuser 4, through the compression paddle 5, and into the subject 6. Incidentally, the optical diffuser 4 is removable from the compression paddle 5, and the presence or absence of the optical diffuser 4 may be selected according to the intended use. The position of the compression paddle 5 in the Z direction is adjustable by means of a moving mechanism (not shown) and may be variously changed according to the size of the subject 6. The compression paddle 5 has the function of making uniform the thickness of the subject 6 in the Z direction by fixing the subject 6 while compressing it. Making the thickness of the subject 6 uniform enables enlargement of the dynamic range of an X-ray image and also enables a reduction in X-radiation exposure. The compression paddle 5 also has the function of guiding the light exiting from the optical diffuser 4 to the subject 6, and also of preventing a decrease in quantity of light entering into the subject 6 by reducing the reflection of light bouncing off the surface of the subject 6.

The detector 10 is a two-dimensional sensor in the XY plane, and has, on its detection surface, a matrix of many sensor elements having sensitivity to X-rays and lights will be described later. Incidentally, a representative example of the size of the detection surface of the detector 10 is dimensions of 250 mm (in the X direction) by 200 mm (in the Y direction). However, the size of the detection surface is not limited to this. Moreover, a representative example of the matrix size of the matrix with the sensor elements is that the matrix has a size of 5000 pixels (in the X direction) by 4000 pixels (in the Y direction). However, the matrix size is not limited to this. The scattered-ray elimination grid 9, the light guide plate 8, and the optical filter 7 are disposed on the top surface of the detector 10 in such a manner as to cover the overall detection surface. The optical filter 7 has the function of cutting off the excitation light entering the detector 10, originating from the light source 3. Also, the optical filter 7 functions to transmit fluorescence emitted from the fluorescent molecular probe administered into the subject 6. A known wavelength selective filter is used as the optical filter 7. Incidentally, the optical filter 7 is removable, and the presence or absence of the optical filter 7 may be selected according to the intended use.

The light guide plate 8 has the function of preventing deterioration in spatial resolution due to the diffusion of the light entering the light guide plate 8 through its top surface in the X and Y directions. The light guide plate 8 also has the function of acting as a protective cover for protecting the scattered-ray elimination grid 9 and the detector 10 from pressure under which the subject 6 is compressed. A known optical fiber plate, microlens array, a viewing angle limiting filter for use in the prevention of a peep into a liquid crystal monitor, or the like can be used as the light guide plate 8. The scattered-ray elimination grid 9 has the function of cutting off X-rays diffused into the subject 6. A focused grid having directivity to an X-ray emitting point of the X-ray tube 1 is used as the scattered-ray elimination grid 9. Incidentally, the scattered-ray elimination grid 9 is capable of transmitting part of the light exiting from the subject 6. Description will be given later with regard to details of the structure of the scattered-ray elimination grid 9.

Description will now be given with regard to operation of the imaging apparatus according to the first embodiment. The imaging apparatus is capable of taking an X-ray image of the subject 6, and, as for optical imaging, the imaging apparatus is also capable of three types of imaging using a fluorescent molecular probe, a luminescent molecular probe, and an optical absorption distribution, respectively. Three types of imaging modes mentioned above will be hereinafter called fluorescence imaging mode, luminescence imaging mode, and optical-absorption imaging mode, respectively. Description will be given below with regard to operations in the imaging modes.

In the fluorescence imaging mode, prior to the imaging, a known fluorescent molecular probe is administered into the body of an examinee. Injection administration, oral administration, or the like is used as a method for administration. Prior to the imaging, moreover, the light source 3, the optical diffuser 4, and the optical filter 7 are disposed. A light source that produces excitation light of an appropriate wavelength in the visible through ultraviolet regions is selected as the light source 3 according to the fluorescent molecular probe for use. An appropriate wavelength selective filter having the properties of cutting off the excitation light and also of transmitting fluorescence emitted from the fluorescent molecular probe is selected as the optical filter 7. Prior to the imaging, further, an examiner sets conditions such as the imaging mode, imaging conditions and imaging procedure mode via the console 102. Here, the fluorescence imaging mode is selected as the imaging mode. Moreover, imaging conditions for X-ray imaging (e.g., the tube voltage and tube current of the X-ray tube, and an imaging time) and an imaging time and others for optical imaging are set as the imaging conditions. Further, the order in which the X-ray imaging and the optical imaging take place is defined as the imaging procedure mode. Incidentally, description will be given later with regard to details of the imaging procedure mode.

At the instant after a lapse of a predetermined time after the administration of the fluorescent molecular probe, first, the examiner positions the subject 6 that is the breast of the examinee, and fixes the subject 6 with it compressed by the compression paddle 5. Then, the examiner enters a command to start the imaging via the console 102. Upon receipt of the command to start the imaging, the imaging controller 101 alternately performs the X-ray imaging and the optical imaging by a method to be described later, in accordance with the setting of the imaging procedure mode. On this occasion, for the X-ray imaging, the imaging controller 101 turns off the light source 3 and also controls the timing of X-ray irradiation by the X-ray tube 1 and the timing of imaging by the detector 10. The imaging controller 101 then takes an X-ray image of the subject 6, and records obtained data in the memory 103. Also, for the optical imaging, the imaging controller 101 turns off the X-ray irradiation by the X-ray tube 1 and also controls the timing of irradiation of the excitation light from the light source 3 and the timing of imaging by the detector 10. The imaging controller 101 then takes an optical image of the subject 6, and records obtained data in the memory 103. Incidentally, plural optical image takings are generally performed as will be described later, and optical images obtained by the takings are recorded in the memory 103. Upon completion of all imaging operations, the arithmetic unit 104 combines the X-ray image with the optical image by a method to be described later, and a resultant image is displayed on the monitor 105.

In the luminescence imaging mode, prior to imaging, a known luminescent molecular probe is administered into the body of the examinee. Injection administration, oral administration, or the like is used as a method for administration. Excitation light is not necessary since the luminescent molecular probe emits light spontaneously. Prior to the imaging, therefore, the light source 3, the optical diffuser 4, and the optical filter 7 are removed. Prior to the imaging, further, the examiner sets the conditions such as the imaging mode, the imaging conditions and the imaging procedure mode via the console 102. Here, the luminescence imaging mode is selected as the imaging mode. Since the setting of the imaging conditions and the setting of the imaging procedure mode are the same as those for the fluorescence imaging mode, description thereof will be omitted. At the instant after a lapse of a predetermined time after the administration of the luminescent molecular probe, the examiner positions the subject 6 by the same procedure as that for the fluorescence imaging mode, and then enters a command to start the imaging. Incidentally, since the following imaging procedure is the same as that for the fluorescence imaging mode except that during the optical imaging the irradiation with the excitation light from the light source 3 does not take place, description thereof will be omitted.

The optical-absorption imaging mode does not require pre-administration of the fluorescent molecular probe or the luminescent molecular probe. Prior to imaging, first, the light source 3 and the optical diffuser 4 are disposed, and the optical filter 7 is removed. A light source that produces light in the near-infrared range to the infrared range, having relatively high blood absorption and high transmission of biological tissue other than blood, is selected as the light source 3. Prior to the imaging, moreover, the examiner sets the conditions such as the imaging mode, the imaging conditions, and the imaging procedure mode via the console 102. Here, the optical-absorption imaging mode is selected as the imaging mode. Since the setting of the imaging conditions and the setting of the imaging procedure mode are the same as those for the fluorescence imaging mode, description thereof will be omitted. Then, the examiner positions the subject 6 and then enters a command to start the imaging via the console 102. Incidentally, since the following imaging procedure is the same as that for the fluorescence imaging mode, description thereof will be omitted.

Figure 2:
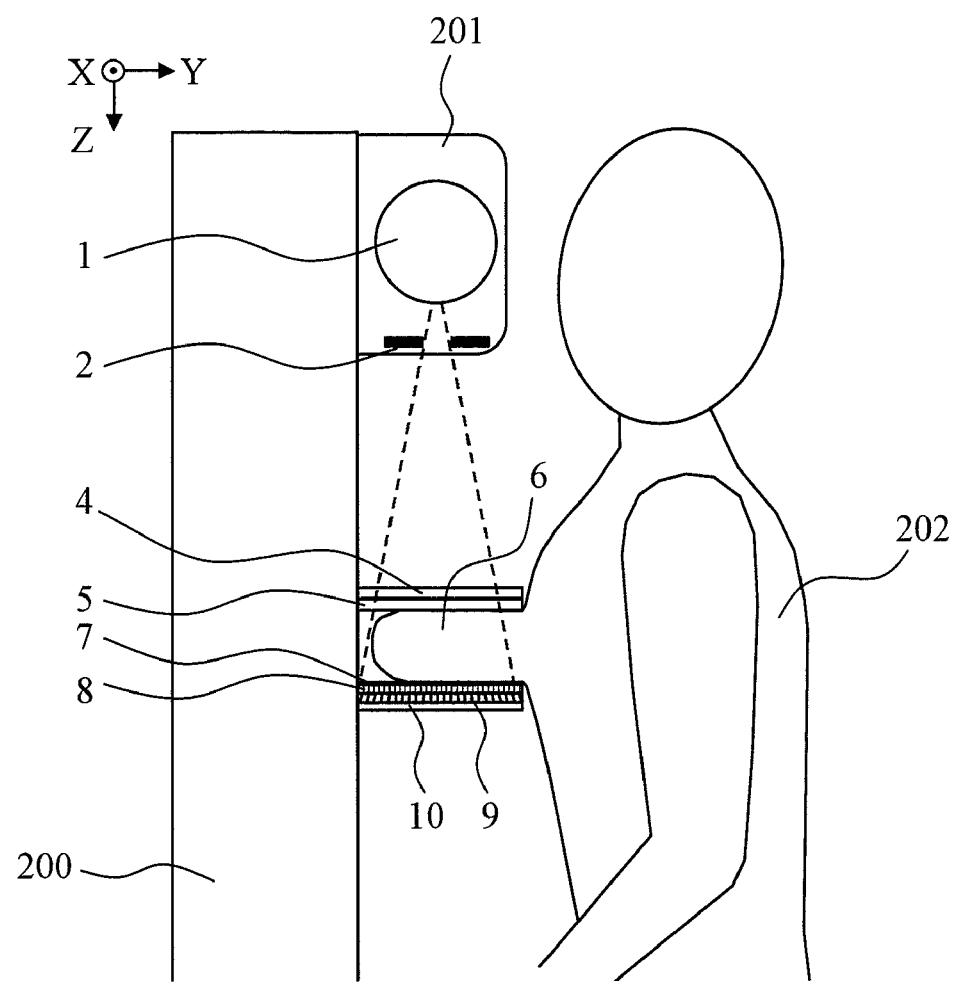
FIG. 2 is an illustration showing a method for positioning a subject.

FIG. 2 is an illustration showing a method for positioning the subject 6 that is the breast of an examinee 202. The X-ray tube 1 and the collimator 2 are fixed to a support pedestal 200 by means of a fixture (not shown), as being covered with a protective cover 201. Also, the compression paddle 5 is supported by the support pedestal 200, and the position of the compression paddle 5 can be shifted in the Z direction by means of the moving mechanism (not shown). Further, the detector 10, the scattered-ray elimination grid 9 and the light guide plate 8 are integrally fixed to the support pedestal 200 by means of a fixture (not shown). The examinee 202, as being in a standing or sitting position, puts the subject 6 that is the breast, on the light guide plate 8, or on the top of the optical filter 7 if the optical filter 7 is used. The examiner adjusts the position of the compression paddle 5 to fix the position of the compression paddle 5 with the subject 6 compressed to an appropriate thickness. Thereby, operation for positioning the subject 6 is brought to an end.

Figure 3:
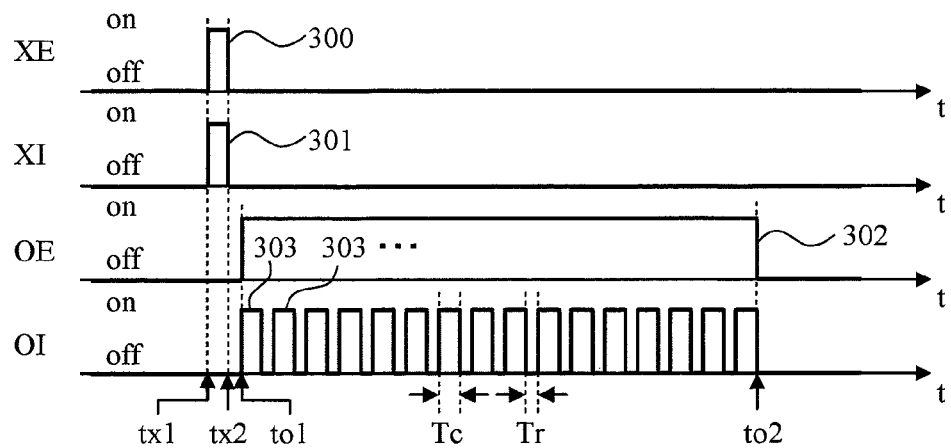
FIG. 3 is a chart showing the timing of X-ray imaging and the timing of optical imaging in X-ray/optical imaging mode that is an example of imaging procedure mode.

FIG. 3 is a chart showing the timing of X-ray imaging and the timing of optical imaging in X-ray/optical imaging mode that is an example of the imaging procedure mode. Incidentally, in FIG. 3, XE denotes the timing of X-ray irradiation by the X-ray tube 1; XI, the timing of X-ray imaging by the detector 10; OE, the timing of light irradiation by the light source 3; and OI, the timing of optical imaging by the detector 10. In FIG. 3, t represents time. Incidentally, since the light source is not used for optical imaging in the luminescence imaging mode, it is not necessary to control the timing OE of light irradiation by the light source 3, shown in FIG. 3.

In the X-ray/optical imaging mode, first, X-ray irradiation 300 takes place between time tx1 and time tx2. In synchronization with the X-ray irradiation 300, X-ray imaging 301 is performed. Incidentally, an X-ray irradiation period (between tx2 and tx1) is generally of the order of a few milliseconds to several hundreds of milliseconds. The X-ray irradiation period mentioned above may be prespecified by the examiner, or may be automatically controlled by a known automatic exposure mechanism (not shown in FIG. 1) during the X-ray imaging. After the completion of the X-ray imaging, optical imaging 303 is repeatedly performed between time to1 and time to2. The interval between repetitions of the optical imaging 303 is defined by a charge period Tc for light signal charge and a signal read period Tr. Representative examples of the periods Tc and Tr are 1 second and 17 milliseconds, respectively. The number of repetitions of the optical imaging 303 is generally set to be of the order of a few times to several hundreds of times according to the intensity of light detected. At this time, an optical imaging period (between to2 and to1) to be examined is of the order of a few seconds to several tens of minutes. Plural images obtained by the optical imaging mentioned above are added as will be described later, and the added image is displayed on the monitor 105 during the optical imaging. Accordingly, while checking the displayed image mentioned above, the examiner may bring the optical imaging to an end, at the time when an appropriate signal is obtained. In the fluorescence imaging mode and the optical-absorption imaging mode that require the light irradiation by the light source 3, continuous light irradiation generally takes place during the optical imaging period (between to2 and to1) mentioned above. In the fluorescence imaging mode, however, pulsed light irradiation may take place for optical imaging using time-resolved fluorescence method. In this case, the timing of pulsed light irradiation is controlled so that irradiation with a pulse of excitation light takes place immediately before the light signal charge period Tc, and that the light signal charge starts after the focusing of the excitation light or background fluorescence after the completion of the pulse irradiation.

Figure 4:
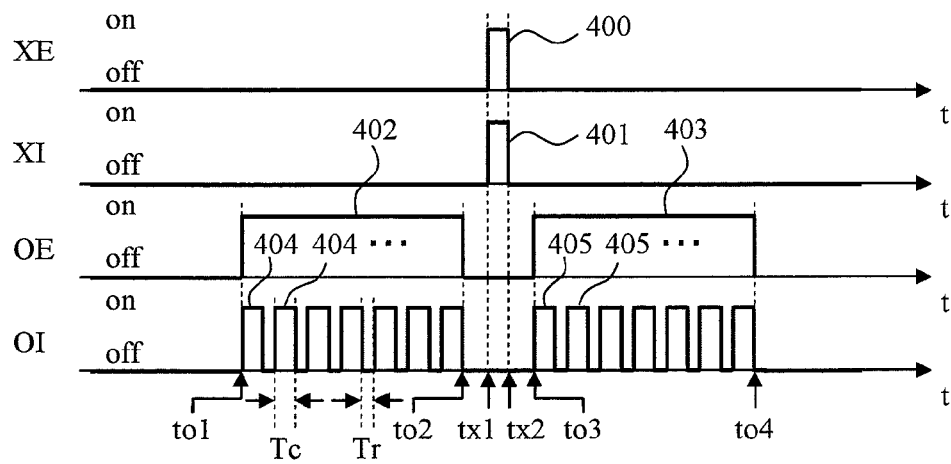
FIG. 4 is a chart showing the timing of X-ray imaging and the timing of optical imaging in optical/X-ray/optical imaging mode that is another example of the imaging procedure mode.

FIG. 4 is a chart showing the timing of X-ray imaging and the timing of optical imaging in optical/X-ray/optical imaging mode that is another example of the imaging procedure mode. The mode shown in FIG. 4 is different from the X-ray/optical imaging mode shown in FIG. 3 in that an X-ray imaging period (between tx1 and tx2) is provided between a first light irradiation period (between to1 and to2) and a second light irradiation period (between to3 and to4). This enables reducing a time lag between the X-ray imaging period and the optical imaging period. Also in FIG. 4, since the light source is not used for optical imaging in the luminescence imaging mode, it is not necessary to control the timing OE of light irradiation shown in FIG. 4.

Figure 5:
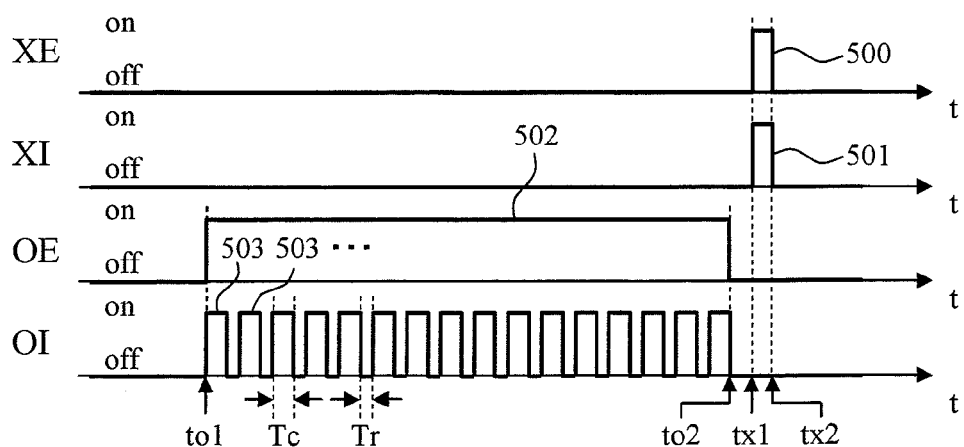
FIG. 5 is a chart showing the timing of X-ray imaging and the timing of optical imaging in optical/X-ray imaging mode that is still another example of the imaging procedure mode.

FIG. 5 is a chart showing the timing of X-ray imaging and the timing of optical imaging in optical/X-ray imaging mode that is still another example of the imaging procedure mode. The mode shown in FIG. 5 is different from the X-ray/optical imaging mode shown in FIG. 3 in that the X-ray imaging period (between tx1 and tx2) is provided after the light irradiation period (between to1 and to2). This enables stopping the X-ray imaging in the event of failure of the optical imaging and thereby preventing the examinee from undergoing ineffective radiation exposure. Also in FIG. 5, since the light source is not used for optical imaging in the luminescence imaging mode, it is not necessary to control the timing OE of light irradiation shown in FIG. 5.

Figure 6:
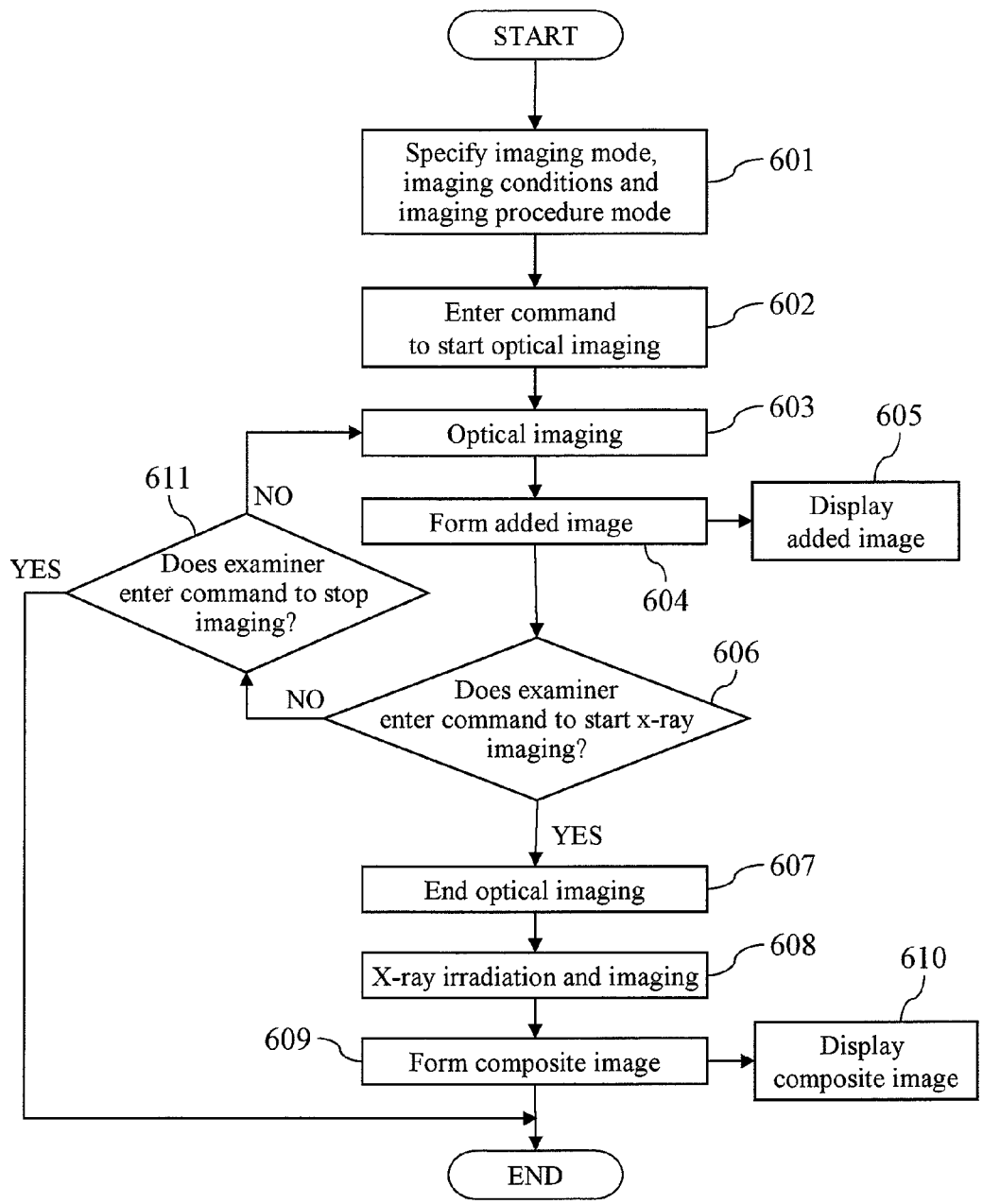
FIG. 6 is an operational flowchart showing a series of operations involved in the optical imaging and the X-ray imaging.

FIG. 6 is an operational flowchart showing a series of operations involved in the optical imaging and the X-ray imaging. Incidentally, in this embodiment, the optical/X-ray imaging mode shown in FIG. 5 is assumed as the imaging procedure mode. Prior to the imaging, first, the examiner specifies the imaging mode, the imaging conditions, and the imaging procedure mode (at step 601). Then, the examiner enters a command to start the optical imaging (at step 602), and the optical imaging is started (at step 603). The optical imaging mentioned above is repeated plural times, and all obtained images are added to form an added image (at step 604). To create such an added image, a new image is added to the previous added image every time the new image is obtained. Also, the added image is updated and displayed every time a new image is created (at step 605).

While checking the added image mentioned above, the examiner enters a command to start the X-ray imaging at the time when the examiner determines that an added image having a desired quantity of light is obtained (at step 606), and the examiner brings the optical imaging to an end (at step 607). At the time when the examiner determines that the added image having the desired quantity of light is not obtained, the examiner may also enter a command to stop the imaging (at step 611) to thereby bring the imaging to forced termination. If the examiner does not enter the command to start the X-ray imaging and the command to stop the imaging, the operation returns to step 603, and the optical imaging is repeated. If the optical imaging ends at step 607, the X-ray irradiation and the X-ray imaging are immediately executed (at step 608). An X-ray image obtained by the X-ray imaging is combined with the added image finally created at step 604 to form a composite image (at step 609). Finally, the composite image is displayed (at step 610), and all operations are brought to an end.

Incidentally, at the above steps 601, 602, 606 and 611, the examiner makes the settings and enters the commands via the console 102 shown in FIG. 1. Also, at the above steps 604 and 609, the arithmetic unit 104 shown in FIG. 1 is used to perform calculations. Incidentally, a purpose-built processor, a known general-purpose processor, or the like is used as the arithmetic unit 104. Further, at the above steps 605 and 610, the monitor 105 shown in FIG. 1 is used for image display.

Figure 7:
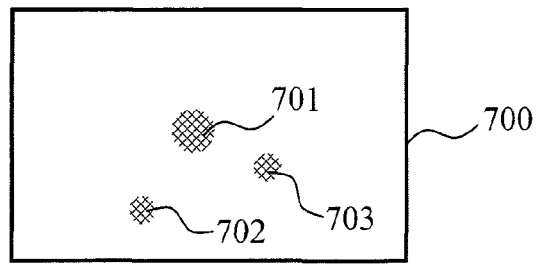
FIG. 7 is a schematic view showing an example of an added image obtained by adding optical images.

FIG. 7 is a schematic view showing an example of the added image obtained by adding optical images. Incidentally, in FIG. 7, a display area 700 represents a display area of the monitor 105. If a region having a high density of the fluorescent molecular probe or the luminescent molecular probe is present within the subject 6, intense light is observed on the outer surface of the subject 6 in the vicinity of the region. Consequently, a light intensity distribution is observed in the added image, and relatively intense light is observed in regions 701, 702 and 703 in the vicinity of a pathological change. However, the spatial resolution in the above-mentioned regions generally lies between a few millimeters and a few centimeters, and the resolution becomes lower as a light emitting source is farther away from the detector 10. Thus, it is difficult to locate the pathological change by use of the above-mentioned optical image alone. On the other hand, in the optical-absorption imaging mode, the light emitted from the light source 3 is intensely absorbed into a blood vessel within the subject 6, and this leads to a decrease in quantity of light observed on the outer surface of the subject 6 in the vicinity of the blood vessel. Thus, the light intensity distribution is observed in the added image, and relatively weak light is observed in the regions 701, 702 and 703 in the vicinity of the pathological change (e.g., nutritional blood vessels concentrating around a cancer cell). As in the case of the fluorescence imaging mode or the luminescence imaging mode, however, the spatial resolution in the above-mentioned regions generally lies between a few millimeters and a few centimeters, and thus, it is difficult to locate the pathological change.

Figure 8:
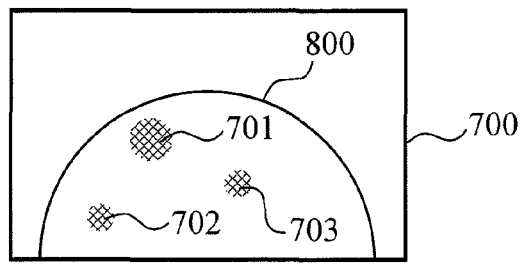
FIG. 8 is a schematic view showing an example of a composite image obtained by combining an X-ray image with the added image of the optical images.

FIG. 8 is a schematic view showing an example of the composite image obtained by combining the X-ray image with the added image obtained by adding the optical images.

Combining the X-ray image with the optical image makes it possible to add detailed information on an external shape 800 or internal tissue of the subject 6. Incidentally, for creation of the composite image, the X-ray image is displayed as a gray-scale image, while optical image information is displayed as a colored image. Thereby, both these pieces of information can be simultaneously displayed. Also, in accordance with user-specified settings, the display of the composite image, the X-ray image alone, or the optical image alone may be freely selected. Combining the optical image with the X-ray image facilitates locating a region having a high probability of occurrence of pathological change. This enables a reduction in the likelihood of a slight pathological change being overlooked and hence an improvement in diagnostic power, and also enables a reduction in a load on a doctor who reads X-rays.

Figure 9:
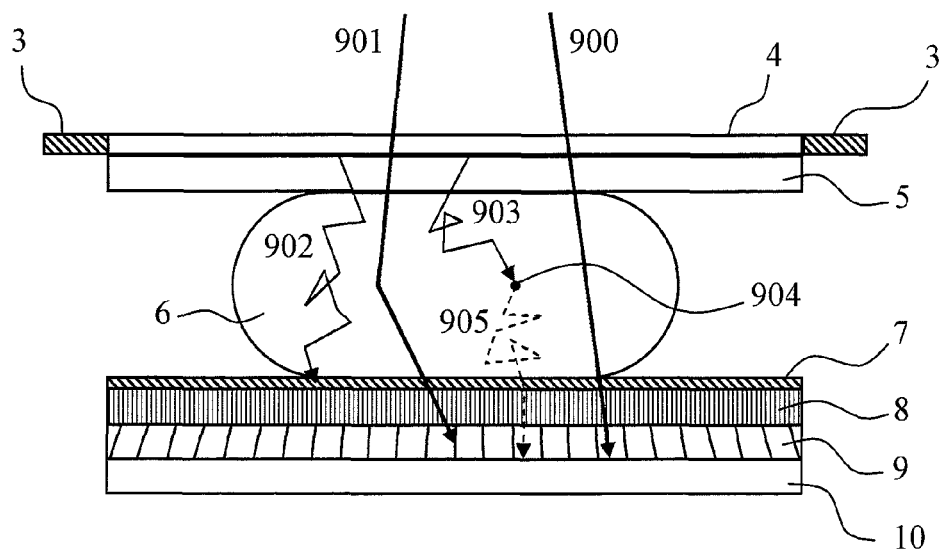
FIG. 9 is a schematic view showing paths through which excitation light, fluorescence and X-rays travel in fluorescence imaging mode.

FIG. 9 is a view showing paths through which the excitation light, the fluorescence, and the X-rays travel in the fluorescence imaging mode. The excitation light emitted from the light source 3 is diffused into the optical diffuser 4. The excitation light is then scattered by known reflecting dots (not shown) printed on the surface of the optical diffuser 4. Thereafter the excitation light travels through the compression paddle 5 and into the subject 6. At this time, one part of the excitation light, namely, excitation light 902, undergoes multiple scattering within the subject 6, and then enters and is absorbed into the optical filter 7. Also, the other part, namely, excitation light 903, is absorbed by a fluorescent molecular probe 904. The fluorescent molecular probe 904 produces fluorescence 905 by using energy obtained by absorption mentioned above. Incidentally, in the process of conversion of the excitation light 903 into the fluorescence 905, the energy is partially converted into heat. Accordingly, the wavelength of the fluorescence 905 is lower than that of the excitation light 903. The excitation light 903 undergoes multiple scattering within the subject 6, then passes through the optical filter 7, the light guide plate 8, and the scattered-ray elimination grid 9. Then, the excitation light 903 is detected by the detector 10.

On the other hand, some of the X-rays emitted from the X-ray tube 1, namely, X-rays 900, pass through the optical diffuser 4, the compression paddle 5, the optical filter 7, the light guide plate 8 and the scattered-ray elimination grid 9. The X-rays 900 are then detected by the detector 10. Also, the rest, namely, X-rays 901, are scattered within the subject 6, then pass through the optical filter 7 and the light guide plate 8, and are absorbed by the scattered-ray elimination grid 9. Incidentally, it is desirable that the thicknesses of the optical diffuser 4, the compression paddle 5 and the light guide plate 8 be reduced to the extent that they present no problem with stiffness properties, in order to minimize X-ray absorption by the optical diffuser 4 and the compression paddle 5 and X-ray and light absorption by the light guide plate 8. Even when the light guide plate 8 in particular is not used, the scattered-ray elimination grid 9 has the function of guiding light, as will be described later. Consequently, the use of the light guide plate 8 is not required, provided that the scattered-ray elimination grid 9 has sufficient stiffness properties.

Figure 10:
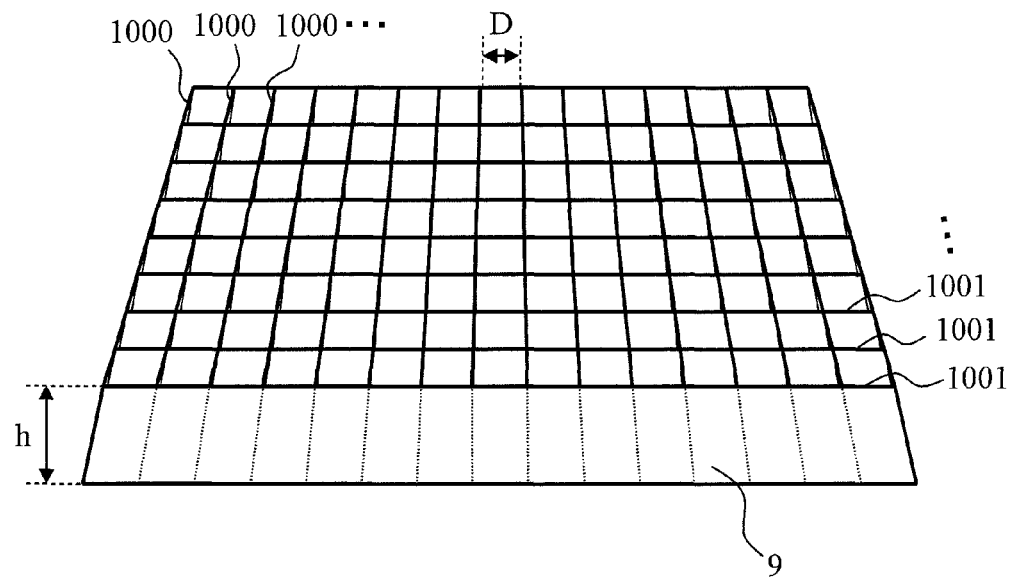
FIG. 10 is a view showing the structure of a scattered-ray elimination grid.

FIG. 10 is a view showing the structure of the scattered-ray elimination grid 9. The scattered-ray elimination grid 9 is formed of septa 1000 that split the incoming X-rays in a horizontal direction and septa 1001 that split the incoming X-rays in a vertical direction, and has a cross-hatched shape. Copper or the like is used as a material for the septa 1000 and 1001. Opening portions of grids are hollow, and the X-rays and light pass through the portions. Incidentally, the hollow portions may be filled with a transparent material such as acrylic so that stiffness is imparted to the scattered-ray elimination grid 9. The septa 1000 and 1001 are obliquely disposed so as to individually have directivity to a focal direction of the X-ray tube 1. Incidentally, a representative example of a grid pitch is 0.45 mm, and a representative example of a grid ratio h/D defined by a width D and a height h of the opening portion is 4.

Figure 11:
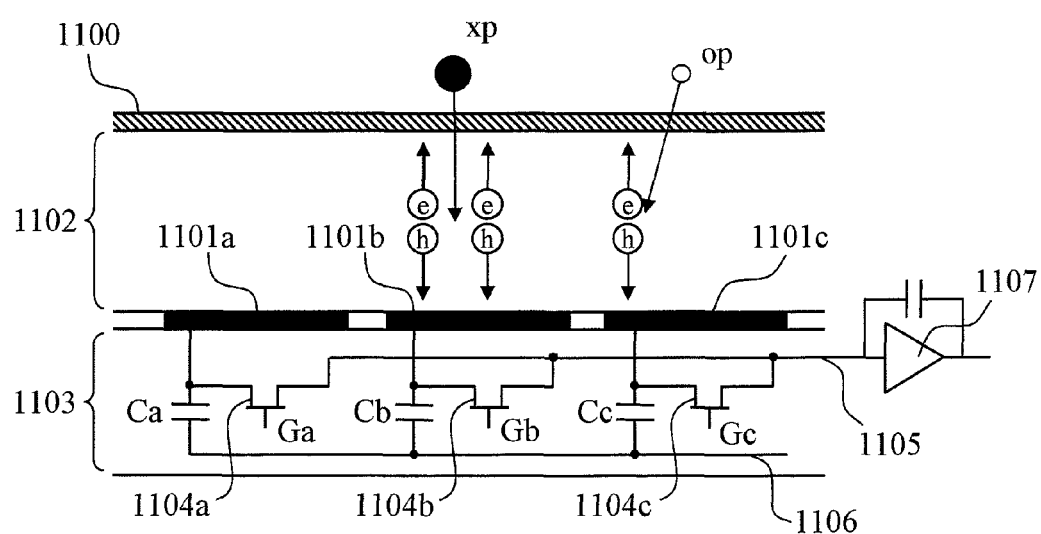
FIG. 11 is a cross-sectional view showing an example of the structure of a detector.

FIG. 11 is a cross-sectional view showing an example of the structure of the detector 10. In this example, the detector 10 is configured of a common electrode 1100, a photoconductor layer 1102, a picture element electrode 1101, a circuit board 1103, and so on. This configuration is equal to the configuration of a known direct conversion type X-ray detector that has been heretofore used in the mammography apparatus or the like, and known materials are used for structural components.

The common electrode 1100 is formed throughout the entire area of the top surface of the photoconductor layer 1102. Transparent ITO is used as a material for the common electrode 1100 in order to ensure light transmission. A representative example of a material for the photoconductor layer 1102 is a-Se, which has sensitivity to X-rays and light. Incidentally, a representative example of the thickness of the a-Se layer is 0.3 mm. Also, other examples of materials for the photoconductor layer 1102 include GdTe, CdZnTe, $HgI_2$, $PbI_2$, CdSe, PbO, CdS, ZnO, and so on. The picture element electrode 1101 is formed in a matrix on the top surface of the circuit board 1103 and constitutes a detecting picture element of the detector 10. Incidentally, a representative example of the pitch of the picture element electrodes is 50 μm. A representative example of the matrix size of the matrix with the picture element electrodes is a 5000- by 4000-pixel matrix. Incidentally, three picture element electrodes 1101a to 1101c disposed in one direction are merely shown in FIG. 11 for sake of simplicity. Also, there is an electrical connection between the a-Se layer and the picture element electrode, since the a-Se layer is formed by vapor deposition of selenium on the circuit board 1103. Also, a voltage is applied between the common electrode 1100 and the picture element electrode 1101 by a power supply (not shown). A representative example of the potential of the common electrode with respect to the picture element electrode 1101 is 3 kV. The circuit board 1103 is formed of a glass board and a device formed thereon by use of a-Si or p-Si by means of known technology. The picture element electrodes 1101a to 1101c have connections to thin film transistor (TFT) switches 1104a to 1104c, respectively, at one end of each switch. Also, the picture element electrodes 1101a to 1101c have connections to capacitances Ca to Cc, respectively, at one end of each capacitance. The other end of each of the capacitances Ca to Cc is connected to a ground line 1106 and is subjected to a ground potential. Also, the other end of each of the TFT switches 1104a to 1104c is connected to an integrating amplifier 1107 through a data read line 1105.

When X-ray photons XP or light photons OP enter the detector 10, they pass through the common electrode 1100, are then detected within the photoconductor layer 1102, and produce electron-hole pairs. It is to be noted that the number of electron-hole pairs produced per light photon OP is one at most, whereas the number of electron-hole pairs produced per X-ray photon XP ranges from the order of several hundreds to the order of several thousands. The electron and hole move toward the electrodes under the influence of an electric field between the common electrode and the picture element electrode. Then, the electron and hole are stored as signal charge in the capacitances Ca to Cc. When gate electrodes Ga to Gc of the TFT switches 1104a to 1104c are sequentially turned on, the signal charge is transferred to the charging amplifier 1107 through the data read line and read out in sequence. Incidentally, for the X-ray imaging that requires high spatial resolution, the signal charge is read out picture element by picture element, as in the case of the above instance. On the other hand, for the optical imaging that does not require high spatial resolution, for example, the gate electrodes Ga to Gc can be simultaneously turned on so that three picture elements of signal charge are added and read out at a time. Such addition of picture elements enables speeding up the reading of signal charge.

Figure 12:
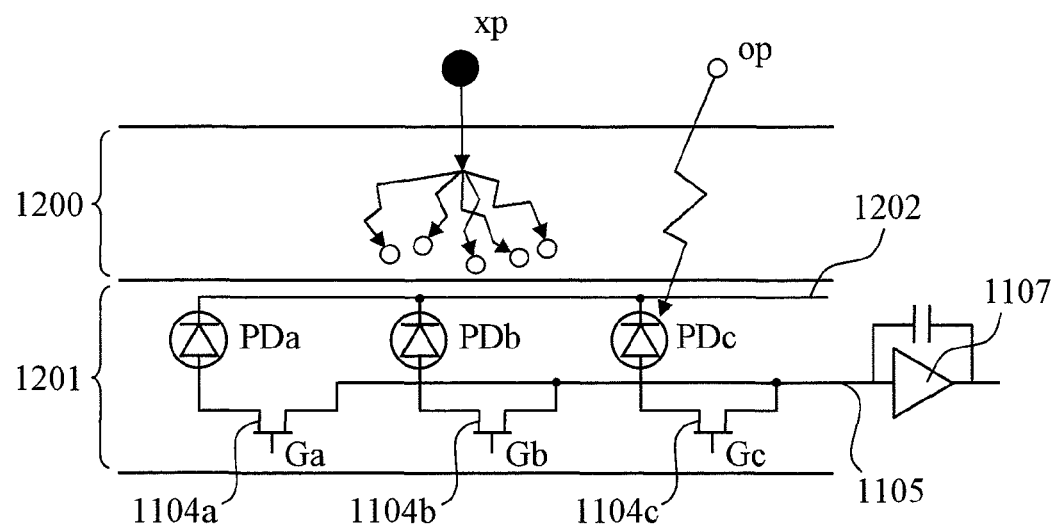
FIG. 12 is a cross-sectional view showing another example of the structure of the detector.

FIG. 12 is a cross-sectional view showing another example of the structure of the detector 10. In this example, the detector 10 is configured of a scintillator layer 1200 and a circuit board 1201. This configuration is equal to the configuration of a known indirect conversion type X-ray detector that has been heretofore used in a digital radiography apparatus or the like, and known materials are used for structural components.

A representative example of a material for the scintillator layer 1200 is GOS ($Gd_2O_2S$), which converts X-rays into light and is also transparent and has the property of transmitting some of light of the visible wavelength range to the infrared wavelength range inclusive. Incidentally, a representative example of the thickness of the GOS layer is 0.3 mm. Also, other examples of materials for the scintillator layer 1200 include CsI, NaI, CWO, BGO, GSO, LSO, YSO, YAP, and so on. Many photodiodes PD are formed in a matrix on the circuit board 1201 and constitute detecting picture elements of the detector 10. Incidentally, a representative example of the pitch of the photodiodes PD is 50 µm, and a representative example of the matrix size of the matrix with the photodiodes PD is a 5000- by 4000-pixel matrix. Incidentally, three photodiodes PDa to PDc disposed in one direction are merely shown in FIG. 12 for sake of simplicity. The circuit board 1201 is formed of a glass board and a device formed thereon by use of a-Si or p-Si by means of known technology. The photodiodes PDa to PDc have connections to the TFT switches 1104a to 1104c, respectively, at one end of each photodiode. Also, the other end of each of the TFT switches 1104a to 1104c is connected to the integrating amplifier 1107 through the data read line 1105. Further, the other end of each of the photodiodes PDa to PDc is connected to a power supply line 1202. A reverse bias voltage is fed to both ends of each of the photodiodes PDa to PDc.

When the X-ray photon XP enters the detector 10, the photon is absorbed into the scintillator layer 1200 and produces about several hundreds through several thousands of light photons. The light photons are detected by the photodiodes PD. Also, when the light photons OP enter the detector 10, they pass through the scintillator layer 1200 and are then detected by the photodiodes PD. Signal charge detected by the photodiodes PDa to PDc is charged into combined capacitance of the photodiodes PDa to PDc, and then read out by controlling the TFT switches 1104a to 1104c by the same procedure as the method described with reference to FIG. 11.

Figure 13:
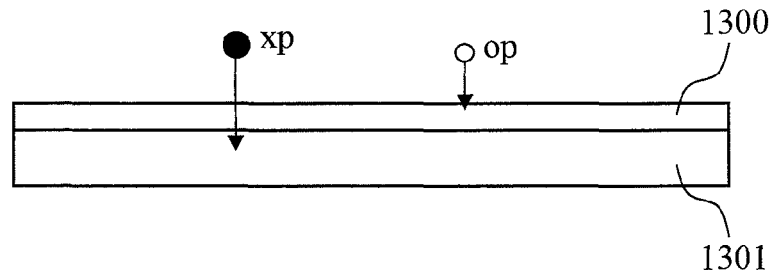
FIG. 13 is a cross-sectional view showing still another example of the structure of the detector.

FIG. 13 is a cross-sectional view showing still another example of the structure of the detector 10. In this example, the detector 10 has a double-layer construction formed of a photodetector 1300 and an X-ray detector 1301, in which the photodetector 1300 is disposed on the front of the X-ray detector 1301. The X-ray photon XP entering the detector 10 passes through the photodetector 1300 and is then detected by the X-ray detector 1301. Also, the light photon OP entering the detector 10 is detected by the photodetector 1300. Incidentally, a photodiode array having the same configuration as the circuit board 1201 shown in FIG. 12 can be used as the photodetector 1300. Also, the X-ray detector having the same configuration as the detectors shown in FIGS. 11 and 12 can be used as the X-ray detector 1301.

Second Embodiment

Figure 14:
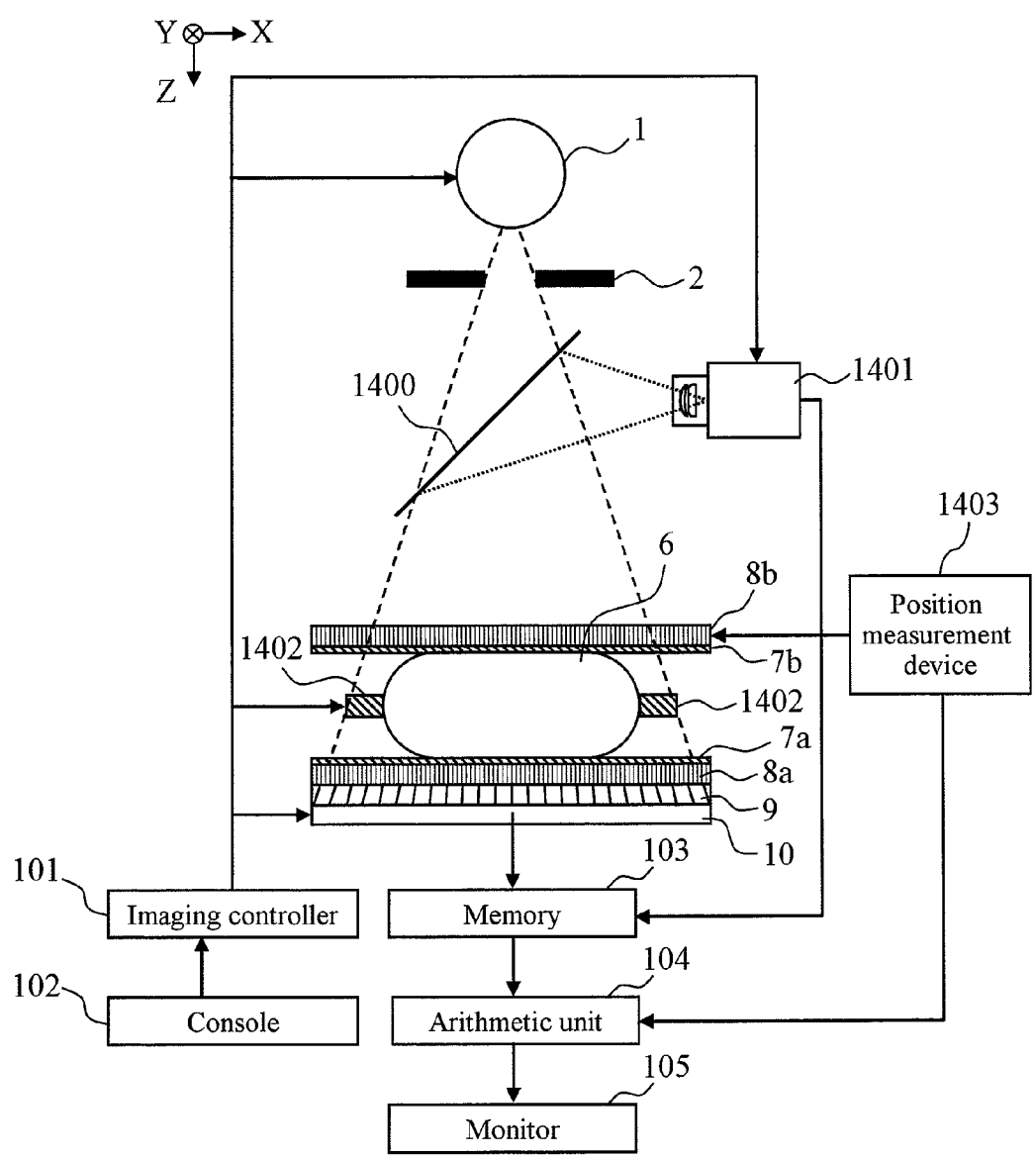
FIG. 14 is a schematic view of an imaging apparatus according to a second embodiment of the present invention.

FIG. 14 is a schematic view of an imaging apparatus according to a second embodiment of the present invention. Incidentally, since the configuration of and operation method for the imaging apparatus according to the second embodiment have many points in common with the first embodiment, description of the common points will be hereinafter omitted, and description will be given only with regard to the points of difference.

Firstly, the points of difference in configuration are as follows. A reflecting mirror 1400 is disposed between the X-ray tube 1 and the subject 6. Moreover, a CCD camera 1401 for taking an image of the subject 6 reflected in the reflecting mirror 1400 is disposed. Also, a light guide 8b is disposed above the subject 6. The light guide 8b has the function of compressing and fixing the subject 6, and also has the function of displaying an optical image outputted from the top surface of the subject 6 on the top portion of the light guide 8b. Incidentally, the light guide 8b is movable in the direction of the Z axis. There is provided a position measurement device 1403 for measuring the position of the bottom portion of the light guide 8b. As will be described later, position information on the light guide 8b measured by the position measurement device 1403 is used for position correction for combination of images, or focus correction for the CCD camera 1401. In FIG. 14, numeral 1402 denotes a light source.

Then, the points of difference in operation method are as follows. The CCD camera 1401 also performs all optical measurements carried out in the fluorescence imaging mode, the luminescence imaging mode and the optical-absorption imaging mode, in synchronization with the optical imaging by the detector 10. All images obtained by the detector 10 and the CCD camera 1401 are recorded in the memory 103. The arithmetic unit 104 combines the X-ray image, the optical image taken by the detector 10, and the optical image taken by the CCD camera 1401 with one another, by using a method to be described later. Also, during the X-ray imaging, the X-rays emitted from the X-ray tube 1 pass through the reflecting mirror 1400, the light guide 8b, and an optical filter 7b, and are then applied to the subject 6. Then, the X-rays pass through the subject 6 and then through an optical filter 7a, a light guide 8a and the scattered-ray elimination grid 9, and are then detected by the detector 10.

The imaging apparatus according to the second embodiment is capable of taking images of light exiting through both the bottom and top surfaces of the subject 6. Thus, the imaging apparatus according to the second embodiment has the advantage of being capable of detecting a pathological change in a relatively upper portion within the subject 6, which is difficult with the imaging apparatus according to the first embodiment. Another great advantage is that DOT method such as is described in David A. Boas et al., "Imaging the Body with Diffuse Optical Tomography," IEEE Signal Processing Magazine, Vol. 18, No. 6, pp. 57-75, (2001) can be applied to the two taken images to thereby perform calculations for tomograms of fluorescence, luminescence and optical absorption distribution within the subject, as will be described later. This enables optical measurement at higher spatial resolution and hence enables a further improvement in diagnostic power by combination with the X-ray image.

Figure 15:
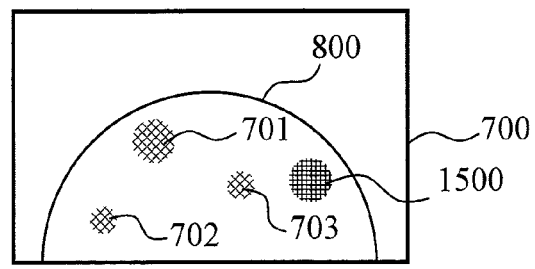
FIG. 15 is a schematic view showing an example of a composite image obtained by combining an X-ray image with an added image of two optical images of the subject taken from the top and bottom surface sides.

FIG. 15 is a schematic view showing an example of a composite image obtained by combining an X-ray image with an added image of two optical images of the subject 6 taken from the top and bottom surface sides. In this example, an optical image 1500 of the subject 6 taken from the top surface side is added to the composite image shown in FIG. 8. Incidentally, for creation of the composite image, the X-ray image is displayed in gray scale, while two pieces of optical image information mentioned above are displayed in different colors. This enables the examiner to grasp depth position information on a pathologically changed part.

Figure 16:
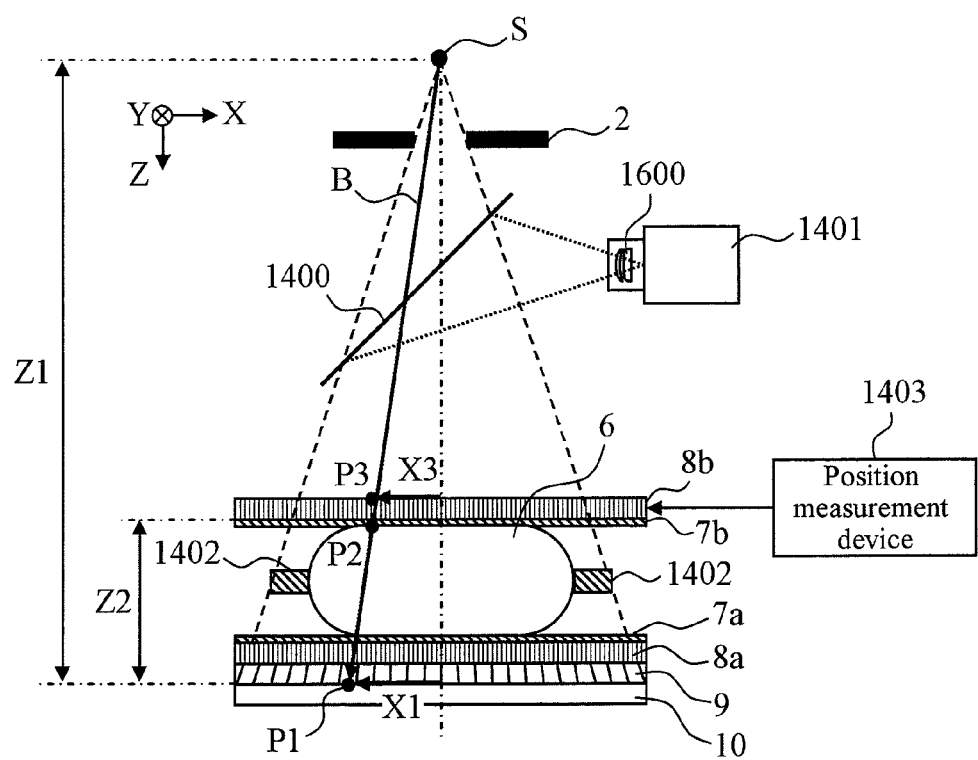
FIG. 16 is a view illustrating a combination position correction method for combining an optical image taken by a CCD camera with the X-ray image taken by the detector.

FIG. 16 is a view illustrating a combination position correction method for combining the optical image taken by the CCD camera 1401 with the X-ray image taken by the detector 10. Light exiting at a surface point P2 on the top surface of the subject is guided by the light guide 8b and then exits at a point P3 substantially directly above the point P2. Consequently, it is necessary to adjust the focus of a lens 1600 of the CCD camera 1401 so as to bring the top surface of the light guide 8b into focus. On this occasion, the position of the light guide 8b varies depending on the size of the subject 6. Accordingly, the adjustment of the focus is performed according to the position of the top surface of the light guide 8b measured by the position measurement device 1403. Also, the light exiting at the point P2 is observed at the point P3 by the CCD camera 1401, whereas an X-ray beam B passing through the point P2 is observed at a point P1 by the detector 10. Now, Equation (1) holds for the relationship between X1 and X3:

$$X1 = X3*Z1/(Z1-Z2) \quad (1)$$

where X1 and X3 represent the positions of the points P1 and P3 in the X direction, respectively, taking an X-ray emitting point S as the starting point; Z1 represents the distance between the X-ray emitting point S and the entrance surface of the detector 10; and Z2 represents the distance between the bottom surface of the light guide 8b and the entrance surface of the detector 10. Likewise, Equation (2) holds for the relationship between Y1 and Y3:

$$Y1 = Y3*Z1/(Z1-Z2) \quad (2)$$

where Y1 and Y3 represent the positions of the points P1 and P3 in the Y direction, respectively.

The optical image taken by the CCD camera 1401 is subjected to scaling using Equations (1) and (2), and thereafter, the optical image is combined with the X-ray image. This enables correcting a misalignment between the optical image and the X-ray image. To perform such correction for any given subject size, the Z2 value can be calculated, based on the measured value determined by the position measurement device 1403.

Figure 17:
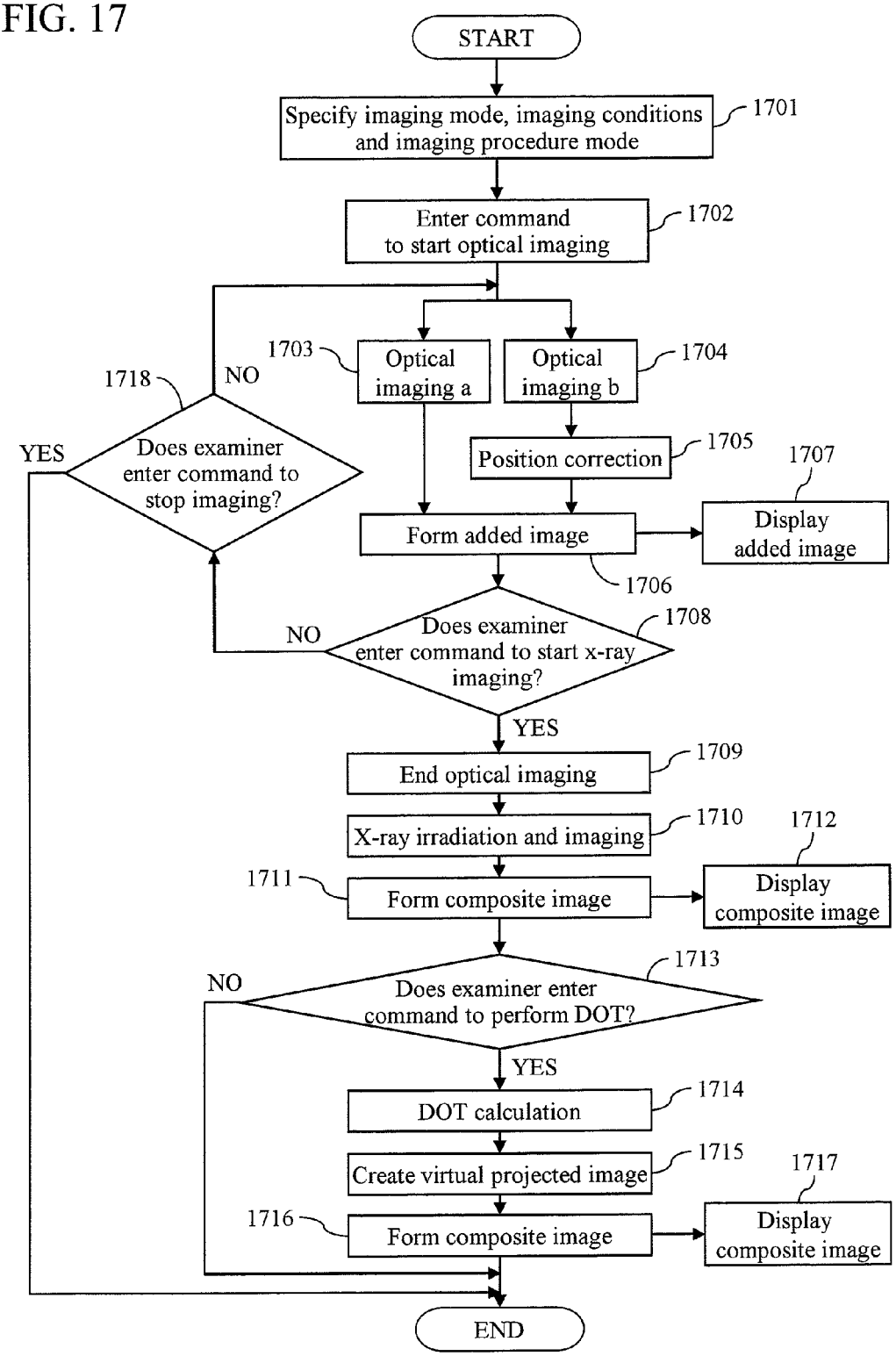
FIG. 17 is an operational flowchart showing a series of operations involved in two types of optical imaging and the X-ray imaging.

FIG. 17 is an operational flowchart showing a series of operations involved in two types of optical imaging and the X-ray imaging. Incidentally, in this embodiment, the optical/X-ray imaging mode shown in FIG. 5 is assumed as the imaging procedure mode. Prior to the imaging, first, the examiner specifies the imaging mode, the imaging conditions, and the imaging procedure mode (at step 1701). Then, the examiner enters a command to start the optical imaging (at step 1702), and optical imaging a by the detector 10 (at step 1703) and optical imaging b by the CCD camera 1401 (at step 1704) are started simultaneously. At this time, an optical image taken by the optical imaging b is subjected to position correction by the method described with reference to FIG. 16 (at step 1705). Then, the optical image subjected to the position correction is added to an optical image taken by the optical imaging a to form an added image. Incidentally, the optical imaging a and the optical imaging b are repeated plural times at the same timing, and all obtained images are added to form an added image (at step 1706). To create such an added image, both the optical image taken by the optical imaging a and the optical image subjected to the position correction at step 1705 are added to the previous added image. Also, the image taken by the optical imaging a and the image taken by the optical imaging b are arranged in different colors and then added to each other. The added image is updated and displayed every time a new image is created (at step 1707).

While checking the added image mentioned above, the examiner enters a command to start the X-ray imaging at the time when the examiner determines that an added image having a desired quantity of light is obtained (at step 1708), and the examiner brings the optical imaging to an end (at step 1709). At the time when the examiner determines that the added image having the desired quantity of light is not obtained, the examiner may also enter a command to stop the imaging (at step 1718) to thereby bring the imaging to forced termination. If the examiner does not enter the command to start the X-ray imaging and the command to stop the imaging, the operation returns to steps 1703 and 1704, and the optical imaging is repeated.

If the optical imaging ends at step 1709, the X-ray irradiation and the X-ray imaging are immediately executed (at step 1710). An X-ray image obtained by the X-ray imaging is combined with the added image finally created at step 1706 to form a composite image (at step 1711). The composite image is displayed (at step 1712). At this time, if the examiner enters a command to perform additional DOT imaging (at step 1713), known DOT calculation such as is described in David A. Boas et al., "Imaging the Body with Diffuse Optical Tomography," IEEE Signal Processing Magazine, Vol. 18, No. 6, pp. 57-75, (2001) or the like is performed to create an optical tomogram of fluorescence, luminescence, optical absorption distribution or the like within the subject 6 (at step 1714). Incidentally, the added image of all optical images obtained by the optical imaging a and the added image of all optical images obtained by the optical imaging b are used for the DOT calculation. On the other hand, if the examiner does not enter the command to perform the additional DOT imaging at step 1713, all operations are brought to an end. For the DOT optical tomogram calculated at step 1714, a virtual projected image is created by use of a method to be described later (at step 1715). Incidentally, the virtual projected image is the virtual projected image of the tomogram, which is formed assuming the X-ray emitting point of the X-ray tube 1 as a virtual projection source. Then, the virtual projected image is combined with the X-ray image to form a composite image by use of the same method as the method of step 1711 (at step 1716). Finally, the composite image is displayed (at step 1717), and all operations are brought to an end.

Incidentally, at the above steps 1701, 1702, 1708, 1718 and 1713, the examiner makes the settings and enters the commands via the console 102 shown in FIG. 14. Also, at the above steps 1706, 1711, and 1714 to 1716, the arithmetic unit 104 shown in FIG. 14 is used to perform calculations. Incidentally, a purpose-built processor, a known general-purpose processor, or the like is used as the arithmetic unit 104. Further, at the above steps 1707, 1712 and 1717, the monitor 105 shown in FIG. 14 is used for image display.

Figure 18:
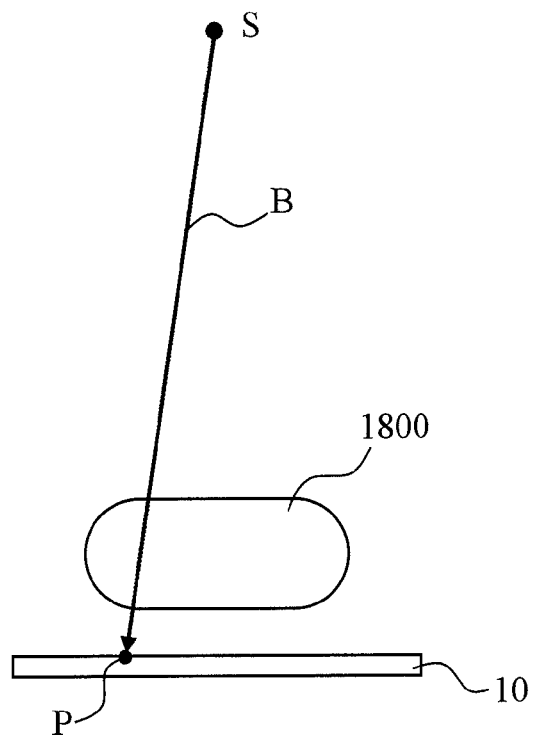
FIG. 18 is a view illustrating an optical tomogram obtained by DOT calculation, and a method for forming a projected image of the optical tomogram with respect to a virtual projection source S.

FIG. 18 is a view illustrating an optical tomogram 1800 obtained by the DOT calculation, and a method for forming a virtual projected image of the optical tomogram 1800 with respect to a virtual projection source S. The virtual projection source S is set at the same position as the X-ray emitting point of the X-ray tube 1. The signal value of the optical tomogram 1800 is integrated on the X-ray beam B emitted from the virtual projection source S to a detecting picture element P on the detector 10. The integrated values are calculated for all detecting picture element points P on the detector 10 to thereby obtain the virtual projected image. The virtual projected image corresponds to the fluorescence, the luminescence, the optical absorption distribution or the like within the subject 6, projected along the same projection path as that for the X-ray imaging. This enables reducing a misalignment between the images on the occasion of combination of the X-ray image and the virtual projected image, and also enables enhancing the spatial resolution of the optical image. As a result, this enables improving the accuracy of detection of pathological change based on the composite image, thus enhancing the diagnostic power.

Third Embodiment

Figure 19:
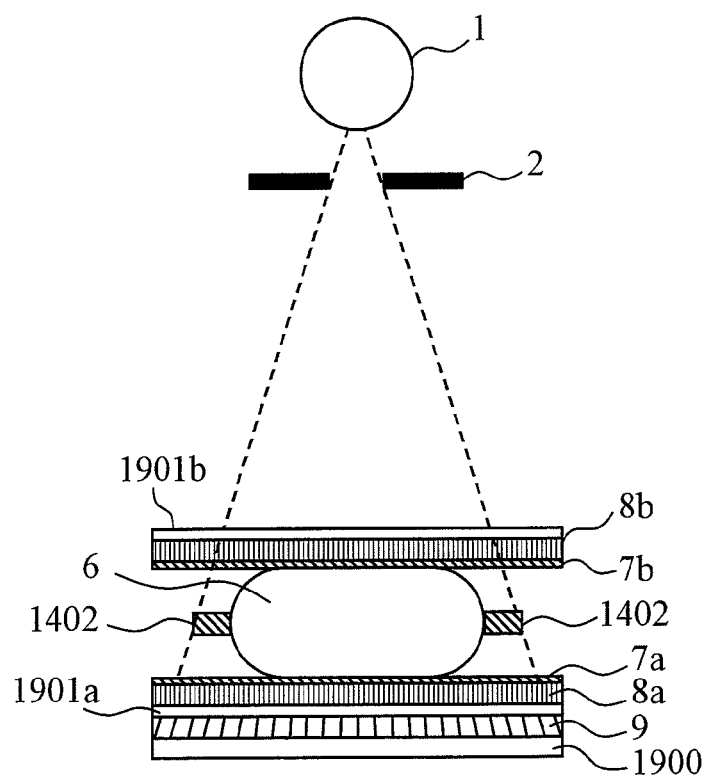
FIG. 19 is a schematic view of an imaging apparatus according to a third embodiment of the present invention.

FIG. 19 is a schematic view of an imaging apparatus according to a third embodiment of the present invention. The imaging apparatus according to the third embodiment is identical in function to, but partially different in configuration from, the imaging apparatus according to the second embodiment. The points of difference are that a detector 1900 is a detector for X-rays only, that a detector 1901a for light only is disposed between the light guide 8a and the scattered-ray elimination grid 9, and that a detector 1901b for light only is disposed on the top surface of the light guide 8b.

The X-rays emitted from the X-ray tube 1 pass through the detector 1901b for light only, the light guide 8b, and the optical filter 7b and then into the subject 6. Also, the X-rays, after passing through the subject 6, pass through the optical filter 7a, the light guide 8a, the detector 1901a for light only, and the scattered-ray elimination grid 9, and are then detected by the detector 1900 for X-rays only. Incidentally, the configuration of the apparatus toward the bottom surface of the subject 6 may be replaced by the configuration using the detector 10, shown in FIG. 1 or 14.

Fourth Embodiment

Figure 20:
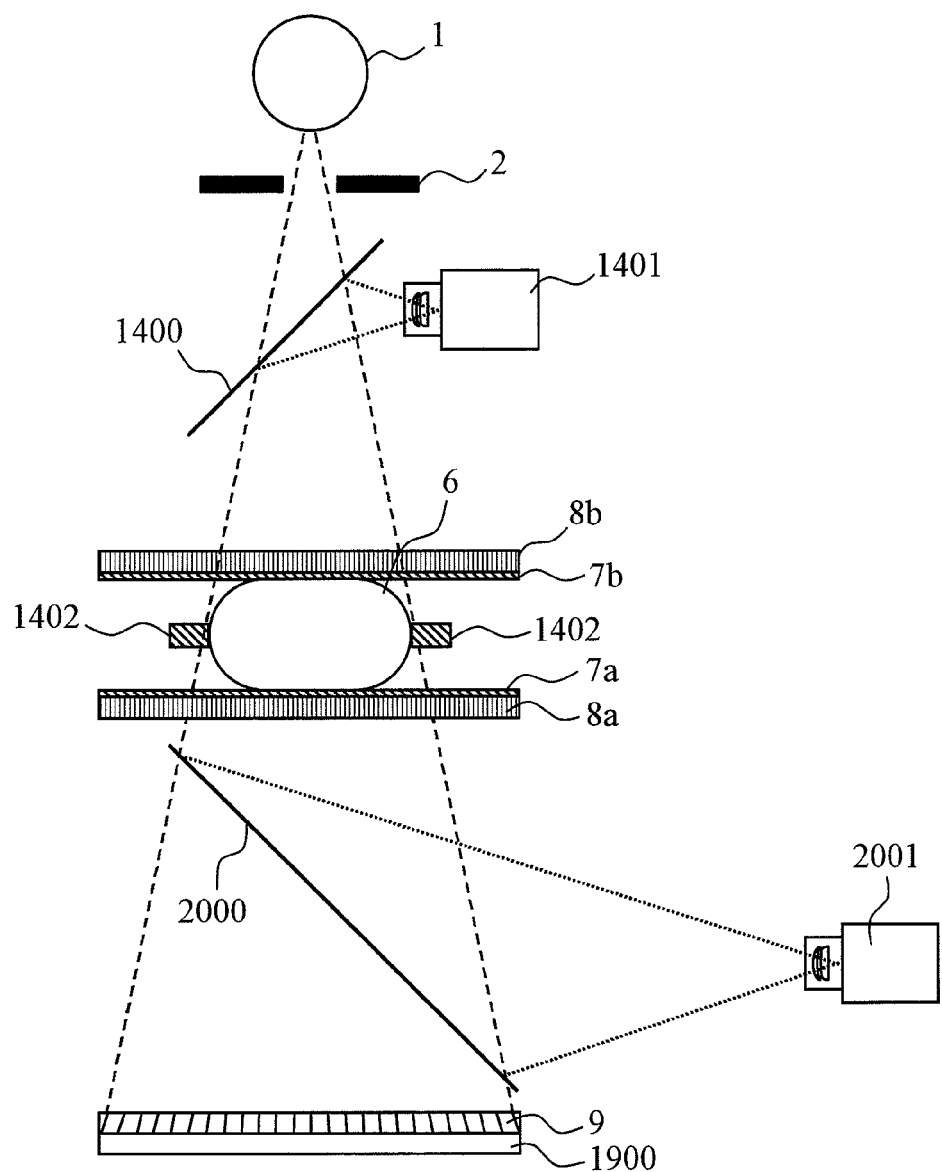
FIG. 20 is a schematic view of an imaging apparatus according to a fourth embodiment of the present invention.

FIG. 20 is a schematic view of an imaging apparatus according to a fourth embodiment of the present invention. The imaging apparatus according to the fourth embodiment is identical in function to, but partially different in configuration from, the imaging apparatus according to the second embodiment. The points of difference are that the detector 1900 is the detector for X-rays only, that a reflecting mirror 2000 is disposed between the light guide 8a and the scattered-ray elimination grid 9, and that a CCD camera 2001 for taking an image of the subject 6 reflected in the reflecting mirror 2000 is disposed.

The X-rays emitted from the X-ray tube 1 pass through the reflecting mirror 1400, the light guide 8b and the optical filter 7b and then into the subject 6. Also, the X-rays, after passing through the subject 6, pass through the optical filter 7a, the light guide 8a, the reflecting mirror 2000 and the scattered-ray elimination grid 9, and are then detected by the detector 1900 for X-rays only. Incidentally, shown in FIG. 20 is the configuration in which the large-sized reflecting mirror 2000 is used in order to prevent unevenness of the X-ray image due to the ends of the reflecting mirror 2000 coming into the visual field of the detector 1900 for X-rays only. However, the reflecting mirror 2000 shown in FIG. 20 may be replaced by the reflecting mirror 2000 smaller than the size of the visual field of the detector 1900 for X-rays only in order to prevent the apparatus from becoming larger in size. Also, the configuration of the apparatus toward the top surface of the subject 6 may be replaced by the configuration using the detector 1901b for light only, shown in FIG. 19.

While the first to fourth embodiments of the present invention have been described above, it is to be understood that the invention is not limited to these embodiments, and various changes and modifications may be made in the invention without departing from the spirit and scope thereof. For example, although the configuration of the apparatus shown in FIG. 2 can make a measurement only on any one of the right and left breasts, which is the subject 6, at a time, two series of taking systems from the X-ray tube 1 to the X-ray detector 10 may be disposed to make measurements on both right and left breasts at a time. This provides the advantages of reducing the time for examination, and also facilitating the adjustment of the timing of start of imaging after the administration of the fluorescent molecular probe or the luminescent molecular probe. Also, the examiner may make settings to perform only any one of the X-ray imaging and the optical imaging. Also, the present invention may be used as intended for a small animal or the like as the subject other than the breast.

What is claimed is:

1. An imaging apparatus comprising:
   an X-ray source that irradiates a subject with X-rays;
   a first detector that detects the X-rays and light, the first detector facing the X-ray source with the subject in between;
   a light guide that guides the light exiting through the outer surface of the subject to a photodetection surface of the first detector; and
   a processing unit that processes the result of detection by the first detector;
   wherein the processing unit processes, as a first signal, an X-ray signal detected by the first detector during an irradiation period in which the X-ray source provides X-ray irradiation, and processes, as a second signal, a light signal detected by the first detector during a period other than the irradiation period.

2. The imaging apparatus according to claim 1, wherein a photodetector of the first detector is made of a photoconductive material having sensitivity to the X-rays and the light.

3. The imaging apparatus according to claim 1, wherein the photodetector of the first detector is made of a scintillator material, and the scintillator material transmits some of light of the visible wavelength range to the infrared wavelength range inclusive.

4. The imaging apparatus according to claim 1, wherein the first detector is formed of two layers: an X-ray detection layer having sensitivity to the X-rays and a photodetection layer having sensitivity to the light.

5. The imaging apparatus according to claim 1, wherein the light guide has the function of eliminating some of the X-rays scattered within the subject.

6. An imaging apparatus comprising:
   an X-ray source that irradiates a subject with X-rays;
   a first detector that detects the X-rays and light, the first detector facing the X-ray source with the subject in between; and
   a processing unit that processes the result of detection by the first detector,
   wherein the processing unit processes, as a first signal, an X-ray signal detected by the first detector during an irradiation period in which the X-ray source provides X-ray irradiation, and processes, as a second signal, a light signal detected by the first detector during a period other than the irradiation period; and
   wherein the processing unit has the function of combining the first signal and the second signal into one image.

7. An imaging apparatus comprising:
an X-ray source that irradiates a subject with X-rays;
a first detector that detects the X-rays and light, the first detector facing the X-ray source with the subject in between;
a light source that irradiates the subject with the light;
a support that supports the subject while being in contact with the subject;
wherein the support has the light guide function of guiding the light emitted from the light source to the subject; and
a processing unit that processes the result of detection by the first detector;
wherein the processing unit processes, as a first signal, an X-ray signal detected by the first detector during an irradiation period in which the X-ray source provides X-ray irradiation, and processes, as a second signal, a light signal detected by the first detector during a period other than the irradiation period.

8. An imaging apparatus comprising:
an X-ray source that irradiates a subject with X-rays;
a first detector that detects the X-rays and light, the first detector facing the X-ray source with the subject in between;
a processing unit that processes the result of detection by the first detector;
wherein the processing unit processes, as a first signal, an X-ray signal detected by the first detector during an irradiation period in which the X-ray source provides X-ray irradiation, and processes, as a second signal, a light signal detected by the first detector during a period other than the irradiation period; and
a second detector that detects the light, the second detector being disposed between the X-ray source and the subject;
wherein the processing unit processes, as a third signal, a signal detected by the second detector during the period other than the irradiation period in which the X-ray source provides the X-ray irradiation, and combines the first signal, the second signal, and the third signal into the one image.

9. The imaging apparatus according to claim 8, further comprising:
a reflecting mirror disposed between the X-ray source and the subject; and
a lens that focuses the light reflected from the reflecting mirror,
wherein the second detector detects the light focused by the lens.

10. The imaging apparatus according to claim 8, further comprising a size measurement means for measuring the size of the subject,
wherein the processing unit has the function of adjusting the combined position of the first signal and the third signal according to the result of measurement by the size measurement means.

11. The imaging apparatus according to claim 8, wherein the processing unit has the function of calculating any one of luminescence and optical absorption intensity distribution within the subject, on the basis of the second signal and the third signal.

12. An imaging apparatus, comprising:
an X-ray source that irradiates a subject with X-rays;
a first detector that detects the X-rays, the first detector facing the X-ray source with the subject in between;
a second detector that detects light, the second detector being disposed between the X-ray source and the subject;
a third detector that detects the light, the third detector being disposed between the subject and the first detector; and
a processing unit that processes the results of detection by the first to third detectors,
wherein the processing unit processes, as a first signal, an X-ray signal detected by the first detector during an irradiation period in which the X-ray source provides X-ray irradiation, and processes light signals detected by the third detector and the second detector during a period other than the irradiation period, as a second signal and a third signal, respectively.

13. The imaging apparatus according to claim 12, wherein the processing unit has the function of combining the first signal, the second signal, and the third signal into one image.

14. The imaging apparatus according to claim 13, further comprising a size measurement means for measuring the size of the subject,
wherein the processing unit has the function of adjusting the combined position of the first signal and the third signal according to the result of measurement by the size measurement means.

15. The imaging apparatus according to claim 12, wherein the processing unit has the function of calculating luminescence or optical absorption intensity distribution within the subject, on the basis of the second signal and the third signal.

16. An imaging apparatus, comprising:
an X-ray source that irradiates a subject with X-rays;
a first detector that detects the X-rays, the first detector facing the X-ray source with the subject in between;
a first reflecting mirror disposed between the X-ray source and the subject;
a first lens that focuses light reflected from the first reflecting mirror;
a second detector that detects the light focused by the first lens;
a second reflecting mirror disposed between the subject and the first detector;
a second lens that focuses the light reflected from the second reflecting mirror;
a third detector that detects the light focused by the second lens; and
a processing unit that processes the results of detection by the first to third detectors,
wherein the processing unit processes, as a first signal, an X-ray signal detected by the first detector during an irradiation period in which the X-ray source provides X-ray irradiation, and processes light signals detected by the third detector and the second detector during a period other than the irradiation period, as a second signal and a third signal, respectively.

17. The imaging apparatus according to claim 16, comprising a size measurement means for measuring the size of the subject,
wherein the processing unit has the function of adjusting the combined position of the first signal and the third signal according to the result of measurement by the size measurement means, and of combining the first signal, the second signal, and the third signal into one image.

18. The imaging apparatus according to claim 16, wherein the processing unit has the function of calculating luminescence or optical absorption intensity distribution within the subject, on the basis of the second signal and the third signal.

* * * * *